United States Patent [19]
Schmidt et al.

[11] Patent Number: 6,072,076
[45] Date of Patent: *Jun. 6, 2000

[54] CONTINUOUS PREPARATION OF ALKYL ESTERS OF (METH)ACRYLIC ACID

[75] Inventors: Willi Schmidt, Ludwigshafen; Matthias Geisendörfer, Neustadt; Alexander Weck, Bühlertal; Toni Dockner, Meckenheim; Holger Herbst, Frankenthal; Gerhard Nestler, Ludwigshafen, all of Germany

[73] Assignee: BASF Aktiengesellschaft, Ludwigshafen, Germany

[ * ] Notice: This patent is subject to a terminal disclaimer.

[21] Appl. No.: 08/789,542

[22] Filed: Jan. 27, 1997

[30] Foreign Application Priority Data

Feb. 6, 1996 [DE] Germany .................. 196 04 253

[51] Int. Cl.⁷ .................................................. C07C 69/52
[52] U.S. Cl. .............................................. 560/205
[58] Field of Search ............................... 560/205

[56] References Cited

U.S. PATENT DOCUMENTS

| | | |
|---|---|---|
| 4,280,009 | 7/1981 | Erpenbach et al. . |
| 4,280,010 | 7/1981 | Erpenbach et al. . |
| 5,606,102 | 2/1997 | Fauconet et al. . |

FOREIGN PATENT DOCUMENTS

| | | |
|---|---|---|
| 0 694 524 | 1/1996 | European Pat. Off. . |
| 25 48 561 | 5/1977 | Germany . |
| 25 52 987 | 6/1977 | Germany . |

*Primary Examiner*—Paul J. Killos
*Attorney, Agent, or Firm*—Oblon, Spivak, McClelland, Maier & Neustadt, P.C.

[57] ABSTRACT

In a process for the continuous preparation of alkyl esters of (meth)acrylic acid by reacting (meth)acrylic acid with alkanols having from 1 to 8 carbon atoms in a homogeneous, liquid, solvent-free phase at elevated temperature and in the presence of an acid esterification catalyst, in which the (meth)acrylic acid, the alkanol and the acid catalyst are fed to a reaction zone, the water formed is removed by rectification during a residence time as constituent of a mixture comprising starting alkanol in a rectification unit (III) superposed on the reaction zone, the distillate obtained is separated into an organic phase comprising alkanol and an aqueous phase comprising water, the organic phase is essentially completely returned to the rectification unit (III), the reaction mixture is discharged from the reaction zone and conveyed into a distillative separation zone comprising further rectification units and in the latter the alkyl (meth)acrylate formed is separated off.

a) (Meth)acrylic acid and alkanol are reacted in a molar ratio of from 1:0.75 to 1:2, b) part of the aqueous phase obtained at the top of the rectification unit (III) is returned to the rectification unit, c) the reaction mixture discharged from the reaction zone is fed to a further rectification unit (I) and in this the reaction mixture is separated into a product (II) comprising the catalyst and a product (I) comprising the alkyl ester of (meth)acrylic acid, remaining alkanol and remaining (meth)acrylic acid, and d) the product (I) is fed to a further rectification unit (II) and in this the alkyl ester of (meth)acrylic acid is separated from the remaining alkanol and from the remaining (meth)acrylic acid and the remaining alkanol and the remaining (meth)acrylic acid are returned to the reaction zone.

22 Claims, 1 Drawing Sheet

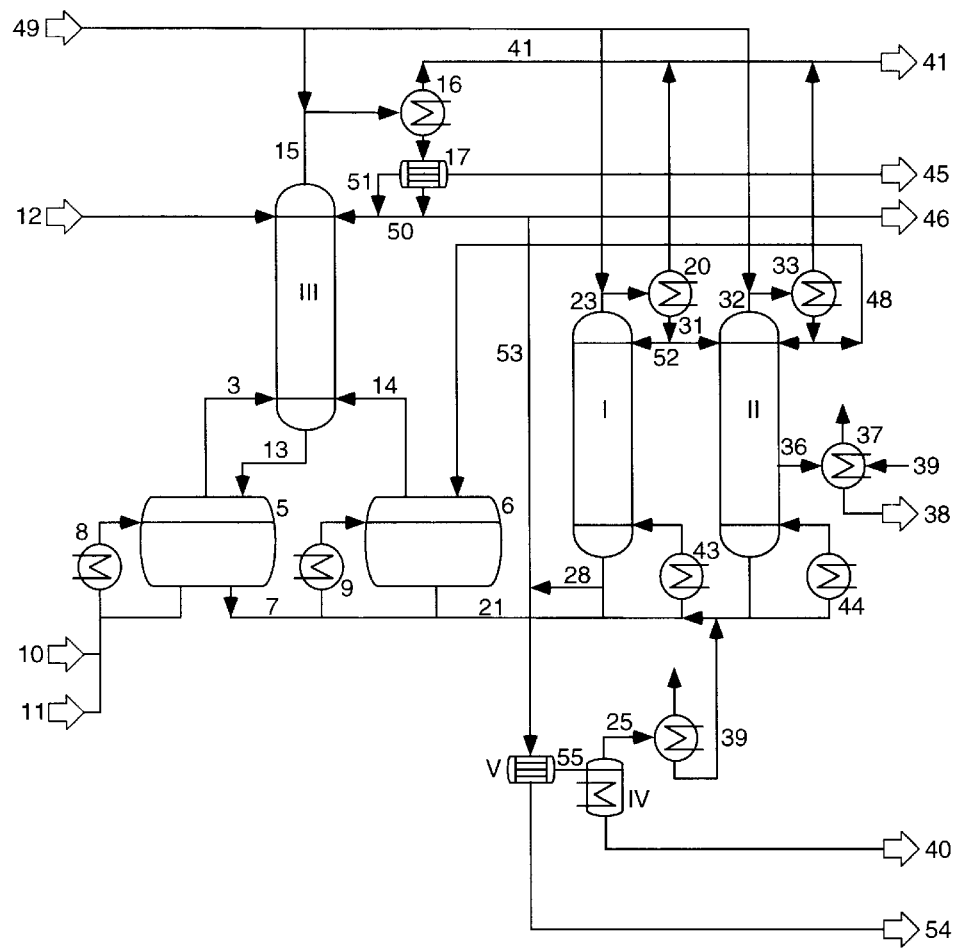

CONTINUOUS PREPARATION OF ALKYL ESTERS OF (METH)ACRYLIC ACID

The invention relates to a process for the continuous preparation of alkyl esters of (meth)acrylic acid by reacting (meth)acrylic acid with alkanols having from 1 to 8 carbon atoms in a homogeneous, liquid, solvent-free phase at elevated temperature and in the presence of an acid esterification catalyst.

In esterifications of alkanol with organic acid, typical equilibrium reactions generally proceed, these reactions being catalyzed by strong acids and, as typical condensation reactions, leading to elimination of water. The esterification equilibrium is usually shifted in the desired direction by removal of the water from the reaction mixture. The removal of the water can be carried out by distillation as constituent of an azeotrope comprising the target ester. The continuous removal of the reaction water from the reaction mixture is then simultaneously accompanied by the separation of the target ester from the reaction mixture. However, the esterification reaction generally proceeds with the water being removed continuously from the reaction mixture, but the major amount of the target ester formed remaining in the reaction mixture.

Examples of esterifications of this type are those in which the reaction water is distillatively removed by addition of an organic solvent as azeotropic entrainer. However, (starting) alkanol used in excess can also serve as such an azeotropic entrainer. Another variant comprises distillatively removing the water as constituent of a heteroazeotrope of target ester/alkanol/water, with the organic phase being essentially completely returned to the esterification.

The product mixtures formed in such esterifications contain essentially the alkyl (meth)acrylate formed, the acid esterification catalyst and by-products formed in the course of the esterification and having boiling points higher than that of the alkyl ester of (meth)acrylic acid. In addition, the product mixtures generally contain polymerization inhibitors and possibly constituents from the group consisting of excess alkanol, excess (meth)acrylic acid, azeotropic entrainers, organic solvents and residual amounts of water. The target ester than has to be separated from these product mixtures. According to Ullmann's Encyclopedia of Industrial Chemistry, 5th edition, Vol. A1, VCH Weinheim, pages 168/169, this separation is generally carried out by the product mixture first being washed with water. The acid esterification catalyst and the excess starting acid go from the organic product phase into the aqueous phase and are thus removed from the product mixture. This separation is normally completed by further washing with aqueous alkali solution.

Subsequently, the remaining alkanol is, as a rule, first removed from the remaining organic phase in a first rectification column and the target ester is then separated off in a further rectification column, in each case via the top of the column.

The disadvantage of such a work-up procedure is, in particular, the formation of large amounts of greatly contaminated wastewater. In addition, the starting acid dissolved in the aqueous alkali solution and the alkanol dissolved therein can generally not be returned directly and technically simply to the esterification, which causes losses of starting materials.

A water-free work-up process is known, for example, from DE-C-25 48 561 for the preparation of 2-ethylhexyl acrylate. In the work-up procedure described therein, excess alkanol and excess starting acid are separated from the product mixture by distillation via the top of the column. In a downstream distillation column, the target ester is then separated by distillation from the bottom product of the preceding distillation column. The bottom product from which the target ester is separated by distillation still contains the acid catalyst of the actual esterification reaction. In addition, the distillative separation of the target ester requires high temperatures even at reduced pressure. This leads, according to our own studies, to dissociation of the compounds formed as by-products in the actual esterification and having boiling points higher than that of the alkyl ester of (meth)acrylic acid into lower-boiling constituents, so that the purity of the target ester thus obtained is not satisfactory.

It is an object of the present invention to provide a process for the continuous preparation of alkyl esters of (meth)acrylic acid which makes possible not only an optimized yield but also milder reaction conditions and thus greatly reduced ether formation, less formation of high boilers, a high space-time yield, an increased flexibility of operation of the plant and also low capital costs owing to a minimized number of equipment items.

The object is achieved starting from the known process for the continuous preparation of alkyl esters of (meth)acrylic acid by reacting (meth)acrylic acid with alkanols having from 1 to 8 carbon atoms in a homogeneous, liquid, solvent-free phase at elevated temperature and in the presence of an acid esterification catalyst, in which the (meth)acrylic acid, the alkanol and the catalyst are fed to a reaction zone, the water formed is removed by rectification during a residence time as constituent of a mixture comprising alkanol in a rectification unit superposed on the reaction zone, the distillate obtained is separated into an organic phase comprising alkanol and an aqueous phase comprising water, the organic phase is essentially completely returned to the rectification unit, the reaction mixture is discharged from the reaction zone and conveyed into a distillative separation zone comprising further rectification units and in the latter the alkyl (meth)acrylate formed is separated off.

The inventive process is characterized by a) reacting (meth)acrylic acid and alkanol in a molar ratio of from 1:0.75 to 1:2, b) returning part of the aqueous phase formed at the top of the rectification unit III to the rectification unit, c) feeding the reaction mixture discharged from the reaction zone to a rectification unit I and in this separating the reaction mixture into a product II comprising the catalyst and a product I comprising the alkyl ester of (meth)acrylic acid, remaining alkanol and remaining (meth)acrylic acid, and d) feeding the product I to a rectification unit and in this separating the alkyl ester of (meth)acrylic acid from the remaining alkanol and from the remaining (meth)acrylic acid and returning the remaining alkanol and the remaining (meth)acrylic acid to the reaction zone.

Both here and below, the term rectification unit is used as a general designation for apparatuses in which heat input generates vapors which rise and are in contact with liquid phase flowing downwards. In general, these are rectification columns having internal fittings to provide efficient contact between liquid and vapor. Such internal fittings are trays such as bubble cap trays, perforated trays, in particular dual flow trays, beds, packings or the like.

To simplify the understanding of the relationships, the various rectification units are designated by Roman numerals. The various, specifically described products are also designated in this way.

The reaction zone consists of one or more reaction regions. In the embodiment of the invention having a plurality of reaction regions, it is advantageous to cascade these. The liquid output stream of one reaction region here forms the feed to the downstream reaction region. This can occur by means of an overflow. If the individual reaction regions are apparatuses separated from one another, there are, taking capital costs into consideration, from 2 to 4 of these. If more than one reaction region is created within one and the same reactor (e.g. by the use of separating sheets of metal), the number of reaction regions can also be greater than 4. In the case of a plurality of reaction regions, the vapors are fed to the reaction regions of a common rectification column whose liquid outflow advantageously goes into the first reaction region. However, it is also possible and in some cases also advisable to superpose a rectification unit on each of a plurality of reaction regions and to return the liquid runback from these rectification units to one or more reaction regions, in each case advantageously into the preceding reaction region.

If this process is carried out using an alkanol having 4–8 carbon atoms, the temperature in the first reaction region is generally 70–150° C., preferably 80–130° C., and in the last region 100–160° C., preferably 110–130° C. The reaction temperature is preferably set in such a way that it rises along the cascade. The pressure in all reaction regions is from 100 mbar to atmospheric pressure, preferably 200 mbar–700 mbar. The pressure is advantageously equal in all reaction regions. The total residence time of the reactants in the reaction regions is generally 0.25–15 hours, preferably 1–7 hours, particularly preferably 1.5–5 hours. The residence time preferably decreases in successive reaction regions.

As acid esterification catalyst, preference is give to using para-toluenesulfonic acid. Its content in the reaction zone, based on the reaction mixture present therein, is advantageously 0.1–10% by weight, preferably 0.1–6% by weight. Other organic sulfonic acids as methanesulfonic acid, benzenesulfonic acid, dodecylsulfonic acid and/or sulfuric acid can likewise be used. Their amount is equimolar to that of para-toluenesulfonic acid. Corresponding mixtures are also possible. The content of catalytically active acid in the liquid phase of the rectification unit I, based on the mixture present therein, can advantageously be from 2.5 to 50% by weight of para-toluenesulfonic acid or an amount equimolar thereto of another organic sulfonic acid and/or sulfuric acid.

In general, both the (meth)acrylic acid and the acid esterification catalyst are fed directly into the reaction zone. The alkanol to be esterified is preferably fed into the reaction zone via the rectification unit III superposed thereon. This rectification unit III can be a rectification column of a known construction type, for example having bubble cap trays or mesh trays. The reaction regions can advantageously consist of reactors having natural or forced-convection vaporizers.

Depending on the alkanol to be esterified, methods of operation differing in detail are appropriate and useful. In the reaction of lower alkanols, the boiling points of the ester and the (meth)acrylic acid are so close together that they can be separated economically by distillation in the rectification unit II only with difficulty.

The esterification of alkanols having more than 4 carbon atoms, in particular having 8 carbon atoms, in which the boiling points of the ester and the (meth)acrylic acid are far apart and therefore it is usually not necessary to feed water as auxiliary forming a low-boiling azeotrope into the rectification unit I, will be described in more detail by means of the example of the esterification of 2-ethylhexanol.

In the esterification of 2-ethylhexanol, part of the aqueous phase obtained at the top of the rectification unit III is returned to this rectification unit. The product mixture discharged from the reaction zone is fed to the rectification unit I. The product mixture introduced into the rectification unit I is in this unit separated into a product I comprising the 2-ethylhexyl ester of (meth)acrylic acid, remaining 2-ethylhexanol and remaining (meth)acrylic acid and into a product II comprising the acid esterification catalyst and components having boiling points higher than the 2-ethylhexyl ester of (meth)acrylic acid. Here, the rectification unit I used is advantageously again a rectification column I. The product mixture discharged from the reaction zone is usually fed into this rectification column in the lower part. The product II is normally obtained from the bottoms of this rectification column and the product I is normally obtained at the top thereof. Part of the product II is advantageously returned to the reaction zone, preferably in the first reaction region, either directly and/or via the rectification unit III. Advantageously, part of the product II is discharged and fed to a distillation unit IV and in this is separated into a product III comprising 2-ethylhexanol, (meth)acrylic acid and the 2-ethylhexyl ester of (meth)acrylic acid and a product IV comprising the acid esterification catalyst and components having boiling points higher than that of the 2-ethylhexyl ester of (meth)acrylic acid.

The product III can then be returned to the rectification unit I and/or to the reaction zone. Acid esterification catalyst can be separated partially or completely from the product II and/or the product IV by extraction with water and the aqueous phase obtained can be partially or completely returned to the reaction zone. For this extraction, use can be made of part of the aqueous phase formed in the rectification unit III. The product I taken from the rectification unit I can be fed to the rectification unit II and in this be separated into a product V comprising remaining 2-ethylhexanol, (meth) acrylic acid and components having boiling points lower than 2-ethylhexyl (meth)acrylate, the target ester 2-ethylhexyl (meth)acrylate and a product VI comprising constituents having boiling points higher than that of 2-ethylhexyl (meth)acrylate. The product V can then be returned to the reaction zone, preferably in the second reaction region, the product VI can be returned to the rectification unit I. The rectification unit II is advantageously configured as a rectification column. Here, the product V can be separated off in the upper part of the rectification column II, the product VI can be taken from the bottom thereof and the 2-ethylhexyl (meth)acrylate can be taken off in vapor form at the side in the lower part.

Further details and advantages of the invention may be found in the example described with the aid of the drawing.

The drawing shows in

FIG. 1 in a process flow diagram a plant for preparing 2-ethylhexyl acrylate.

The rectification columns are provided with Roman reference numerals. In addition, in the interests of clarity, the product designations, generally provided with Roman numerals are inserted by names in this specific example.

The plant shown has three rectification columns I, II, III and a stirred vessel IV. In addition, it is provided with two esterification reactors 5 and 6 which are connected in series by means of a line 7 and thus form a reaction cascade. Convection vaporizers 8 and 9 are connected to the reactors 5 and 6.

The esterification reaction of 2-ethylhexanol and acrylic acid was carried out in the two-stage esterification cascade consisting of the two reactors 5 and 6, which had equal volumes. Acrylic acid via a line 10 and p-toluenesulfonic acid as catalyst via a line 11 were fed to the reactor 5 via the convection vaporizer 8. The reaction component 2-ethylhexanol was fed via a line 12 to the top of a distillation column III whose lower end was connected via a line 13 to the reactor 5. The vapor formed in the esterification in the reactors 5 and 6 and containing the water of reaction was fed via lines 3 and 14 to the distillation column III which had 20 bubble cap trays and was operated at a pressure of 270 mbar. This pressure was maintained by means of a line 15, which led to a condenser 16, via a line 41 leading to a vacuum pump. The condensate formed in the condenser 16 was separated into two liquid phases in the separator 17. Octenes separated off were discharged through line 45. Water of reaction was discharged through the line 46.

Since the starting materials were fed at ambient temperature to the reactor 5 and a large amount of water is formed in the reaction, a high heat input into the first reactor 5 is necessary for maintaining a reaction temperature of 110° C. This makes possible the use of an external convection vaporizer 8. The bottom product discharged from the reactor 5 via line 7 was fed via a further convection vaporizer 9 to the second reactor 6 in which a temperature of 120° C. was set. The second vaporizer 9 was configured as a convection vaporizer to ensure a circulated amount sufficient for mixing the contents of the reactor, despite significantly lower heat input. Here too, lean air was added as co-stabilizer. Matched to the decreasing acrylic acid and water concentrations, the second reactor 6 was operated at elevated temperature. The bottom product formed in reactor 6 was discharged through line 21. The entire reaction mixture discharged, which comprises the target product, i.e. the 2-ethylhexyl acrylate formed, and all lower-boiling starting materials and by-products, was conveyed via line 21 and a further convection vaporizer 43 into the lower part of a rectification column I which was configured as an enrichment column and, being fitted with ten dual flow trays, served to separate off the high boilers. The target product, namely 2-ethylhexyl acrylate, and all lower-boiling starting materials and by-products were discharged via the top through line 23 and, after flowing through a condenser connected to the vacuum line 41, were fed via line 31 to the top of a pure column II operated as a stripper column.

The column I for separating off the high boilers was operated at a bottom pressure of 100 mbar and a top pressure of 70 mbar. The temperature was 150° C.

The bottoms obtained in the column I for separating off high boilers were discharged via a line 28, cooled to 50° C. and fed to an extraction unit. With addition of part of the esterification water through line 53, the content of para-toluenesulfonic acid in the organic phase was reduced to 1.5%, which is optimal for the separation. The water stream produced, which was loaded with up to 30% of para-toluenesulfonic acid, was taken off through line 54, the organic phase was taken off through line 55 and fed to a distillation unit IV. In this, the product still present was first vaporized batchwise at 180° C. and a pressure of 60 mbar. Subsequently, the residue having a high content of p-toluenesulfonic acid and oxy-esters was cracked to give starting materials, tuarget product, water and the octenes formed as by-product. The combined top product from the cracking step was taken off via line 25, liquefied and returned via line 39 to the bottom of the high-boiler separation. The remaining viscous residue was taken off through line 40 and disposed of in a residue incineration facility.

From the product fed via line 31 to the top of the pure column II, the starting materials and relatively low-boiling secondary components still present were taken off via line 32 and fed to a condenser 33. The condensate formed here was returned via line 48 to the second stage 6 of the esterification cascade. The liquid phase of the column II was heated by means of a convection vaporizer 44 similar to those used in the esterification.

The pure product 2-ethylhexyl acrylate was taken off in vapor form via line 36 and fed via a trickle-type demister to the condenser 37 in order to avoid color number problems and to make possible the change in stabilization of the product from phenothiazine as process inhibitor to hydroquinone monomethyl ether as storage stabilizer. The pure product was discharged via line 38 and the storage stabilizer was fed in via line 39. The phenothiazine used as process inhibitor was fed via line 49 to the tops of the rectification columns I, II, III.

In the following, a description will now be given of a specific example which has been carried out using an experimental apparatus as shown in the drawing. In this example, use was made of two esterification reactors 5 and 6 each having a utilizable capacity of 2 l and superposed by a glass tray column having a diameter of 50 mm and equipped with 20 bubble cap trays and a phase separator at the top of the column. The operating pressure was 270 mbar. Convection vaporizers were used for heating the esterification reactors. At a residence time of 4 hours, acrylic acid was reacted with 2-ethylhexanol in the stoichiometric ratio with addition of 1.5% by weight of aqueous p-toluenesulfonic acid solution and continuous removal by distillation of the water of reaction formed, to give 2-ethylhexyl acrylate (EHA). The temperature in the first esterification reactor 5 was 110° C., in the second esterification reactor 6 the temperature was 120° C. In the discharge from the first reactor 5, an EHA concentration of 70% by weight was achieved, and a concentration of 82% by weight was achieved in the discharge of the second reactor 6. Low-boiling secondary components (mainly octenes formed in the cracking step) were concentrated in the top of the esterification column III to such an extent that the waste stream taken off via line 45 contained only <10% of components of value, i.e. 2-ethylhexanol and 2-ethylhexyl acrylate. By means of aqueous column runback, two liquid phases were generated over the entire column height. This enabled the acrylic acid concentration at the top of the column to be reduced to <100 ppm. The water of esterification formed in a stoichiometric amount contained about 1.5% of organic compounds (mainly 2-ethylhexanol and octenes) at equilibrium.

The esterification product through line 21 was freed of the catalyst acid and the high boilers formed in a laboratory column I having a diameter of 50 mm and 10 dual flow trays and fitted with a convection vaporizer and heat exchanger. 5% of the raw ester flowing in was, at a reflux ratio of 0.5, taken from the bottom of the column as high-boiler discharge and fed via an extraction stage to the cracking step; the remainder was taken off as top product free of high boilers (oxyesters <10 ppm). The feed was directly into the bottom of the column and the column I was operated as a pure enrichment column. At a pressure at the top of 80 mbar, a maximum bottom temperature of 150° C. could be maintained. The top product free of high boilers was, in a laboratory column II having a diameter of 50 mm and fitted with 25 dual flow trays, separated into a top fraction containing the starting materials acrylic acid and 2-ethylhexanol and also 50% by weight of 2-ethylhexyl acrylate and the pure product at a pressure at the top of 80 mbar and a maximum bottom temperature of 140° C. The top fraction was returned to the second esterification reactor 6. The pure product was taken off in vapor form, free of high boilers and process stabilizers, from the column bottoms which were heated by means of a convection vaporizer and was liquefied in a condenser regulated by inert blanketing. This achieved a content of >99.8% by weight of 2-ethylhexyl acrylate. Accumulation of high-boiling trace components in the column bottoms was prevented by a liquid bottom bleed into the bottom of the high-boiler separation of 2% of the liquid flowing to the laboratory column II. The bottom product from the high-boiler separation was, after partial extraction of the catalyst acid using water, evaporated at 60 mbar and a maximum temperature of 180° C. in a cracking vessel IV, which was operated batchwise, to 20% of its original mass. The residue formed contained, apart from the catalyst acid p-toluenesulfonic acid, a high concentration of high boilers which could not be cracked and vaporized. This residue could not be further utilized in the process and was taken off. The top product consisting to the extent of 80% of EHA, from 10 to 12% of octenes and acrylic acid, water and 2-ethylhexanol was precipitated in a heat exchanger and returned to the bottom of the high-boiler separation.

In continuous, steady-state operation of this experimental plant, a yield of 98% based on starting materials was able to be achieved. Only 2% of the starting materials used were lost as by-products.

The stabilizer solution used was a 2% strength phenothiazine solution in 2-ethylhexanol, which was in each case metered into the top condensers of the individual process stages in an amount of 100 ppm, based on the respective feed stream of the stage. All natural convection vaporizers were exposed to air as costabilizer.

A particular advantage of the above-described process is the separation of all high-boiling secondary components and particularly the catalyst from the esterification product in column I. This reliably avoids redissociation of the high boilers and/or the target product in the liquid phase of the pure column II into starting materials and thus contamination of the pure product with low-boiling dissociation products and particularly acrylic acid.

If, as is customary in conventional processes, the components having boiling points lower than that of the target ester (in particular acrylic acid and starting alkanol) are first separated from the esterification product, it is not possible, owing to the dissociation reactions then occurring in the liquid phase of the pure column in the presence of catalyst and high boilers, to obtain pure product free of low boilers and particularly acrylic acid, as was demonstrated by the example described below:

Esterification product taken from line 21 was first freed of all secondary components having boiling points lower than that of the target ester and also of the starting materials acrylic acid and 2-ethylhexanol in column I. The raw ester which was free of low boilers but contaminated with high boilers and particularly the catalyst was then taken from the bottom of column I and rectified in a laboratory column having a diameter of 50 mm and fitted with 25 dual flow trays at a reflux ratio of 2. The raw ester taken off at the top of this column was contaminated with 1400 ppm of acrylic acid, although the raw ester fed in was free of acrylic acid; i.e. the acrylic acid found in the target ester could only have arisen by means of dissociation reactions in the liquid phase of the column. However, removal of the acrylic acid by distillation is not possible when the pure ester is obtained as top product, since acrylic acid is a low boiler in comparison with the target ester.

From the above-described experimental results and further studies, it was able to be deduced that it is advantageous to operate the two esterification reactors 5 and 6 at pressures of from 180 to 500 mbar, preferably from 180 to 350 mbar. The temperature in the first reactor 5 can be from 80 to 120° C., in the second reactor 6 from 100 to 140° C. As catalyst for the esterification reaction in the reactors 5 and 6, acid catalysts, in particular organic sulfonic acids and here especially p-toluenesulfonic acid in an amount of from 0.1 to 4% by weight, preferably from 0.5 to 2% by weight, have been found to be particularly advantageous.

The residence time of (meth)acrylic acid and alkanol in the reactors is from 0.5 to 8 hours, preferably from 1 to 6 hours. From the raw ester fed through line 21 to the rectification column I an amount of <10% by weight, preferably <5% by weight, can, at a reflux ratio of 0.5, be taken from the bottom of the column as a high-boiler bleed and fed via an extraction stage to the cracking step. The pressure at the top of the column I can be from 50 to 400 mbar, preferably <120 mbar. The maximum bottom temperature of this column is preferably $\leq 150°$ C. The top product of column I, which was free of high boilers and was fed via line 31 to column II, can be processed there at a pressure at the top of from 50 to 400 mbar, preferably at a pressure of <120 mbar, and at a bottom temperature of <140° C. With optimum setting of the abovementioned values, it is possible to take off, through line 36, a product containing >99.8% by weight of pure product, in the case of the example of 2-ethylhexyl acrylate.

We claim:

1. A process for the continuous preparation of alkyl esters of (meth)acrylic acid by reacting (meth)acrylic acid with alkanols having from 1 to 8 carbon atoms in a homogeneous, liquid, solvent-free phase at elevated temperature and in the presence of an acid esterification catalyst, in which the reaction mixture comprising (meth)acrylic acid, the alkanol and the catalyst are fed to a reaction zone I, the water formed is removed by rectification during a residence time as a constituent of a mixture comprising alkanol in a rectification unit (III) superposed on the reaction zone, the distillate obtained is separated into an organic phase comprising alkanol and an aqueous phase comprising water, the organic phase is essentially completely returned to the rectification unit (III), the reaction mixture is discharged from the reaction zone and conveyed into a distillative separation zone comprising further rectification units and in the latter the alkyl (meth)acrylate formed is separated off, wherein a) (meth)acrylic acid and alkanol are reacted in a molar ratio of from 1:0.75 to 1:2, b) part of the aqueous phase obtained at the top of the rectification unit (III) is returned to the rectification unit (III), c) the reaction mixture discharged from the reaction zone is fed to a further rectification unit (I) wherein the reaction mixture is separated into a product (II) comprising the catalyst and a product (I) comprising the alkyl ester of (meth)acrylic acid, remaining alkanol and remaining (meth)acrylic acid, and d) the product (I) is fed to a further rectification unit (II) wherein the alkyl ester of (meth)acrylic acid is separated from the remaining alkanol and from the remaining (meth)acrylic acid and the remaining alkanol and the remaining (meth)acrylic acid are returned to the reaction zone.

2. A process as claimed in claim 1, wherein the reaction zone comprises a cascade of at least two reaction regions connected in series and the product stream of one reaction region forms a feed stream of a downstream reaction region, and wherein the cascade comprises from 2 to 4 reaction regions separated in space from one another.

3. A process as claimed in claim 2, wherein the temperature in the first reaction region is 70–150° C., and in the last region is 100–160° C., and rises along the cascade.

4. A process as claimed in claim 2, wherein the pressure in all reaction region is from 100 mbar to atmospheric pressure, and is the same in all reaction regions.

5. A process as claimed in claim 1, wherein the total residence time of the reactants in the reaction regions is from 0.25 to 15 hours, and wherein the residence time decreases in successive reaction regions.

6. A process as claimed in claim 1, wherein the rising vapors from the reaction regions are fed to the rectification unit (III) whose liquid runback is returned only to the first reaction region.

7. A process as claimed in claim 1, wherein the catalyst used is paratoluenesulfonic acid or other organic sulfonic acids or sulfuric acid, and wherein the content of catalytically active acid in the reaction zone, based on the reaction mixture present therein, is from 0.1 to 10% by weight, of para-toluenesulfonic acid, or an amount equimolar thereto of organic sulfonic acid or sulfuric acid, and wherein the content of catalytically active acid in the liquid phase of the rectification unit I, based on the mixture present therein, is from 2.5 to 50% by weight of paratoleunesulfonic acid or an amount equimolar thereto of another organic sulfonic acid or sulfuric acid.

8. A process as claimed in claim 1, wherein the alkanol to be esterified is 2-ethylhexanol, both the (meth)acrylic acid and the catalyst are fed directly to the reaction zone, and the starting alkanol to be esterified is fed to the reaction zone via the rectification unit (III).

9. A process as claimed in claim 1, wherein the rectification unit (III) is a rectification column, and the reaction regions comprise reactors with convection vaporizers.

10. A process as claimed in claim 8, wherein the product mixture introduced into the rectification unit (I) is, in the rectification unit (I), separated into a product (I) comprising the 2-ethylhexyl ester of (meth)acrylic acid, remaining 2-ethylhexanol and remaining (meth)acrylic acid and into a product (II) comprising the catalyst and components having boiling points higher than that of the 2-ethylhexyl ester of (meth)acrylic acid.

11. A process as claimed in claim 10, wherein the rectification unit (I) is a rectification column (I), the product mixture discharged from the reaction zone is fed to the lower part of the rectification column (I), the product (II) is obtained at the bottom of the rectification column (I) and the product (I) is obtained at the top of the rectification column (I), and wherein part of the product (II) is returned to the reaction zone, either directly or via the rectification unit (III).

12. A process as claimed in claim 11, wherein part of the product (II) is discharged and fed to a distillation unit (IV) and in this is separated into a product (III) comprising 2-ethylhexanol, (meth)acrylic acid and the 2-ethylhexyl ester of (meth)acrylic acid and a product (IV) comprising the catalyst and components having boiling points higher than that of the 2-ethylhexyl ester of (meth)acrylic acid, wherein the product (III) is returned to the rectification unit (I) or the reaction zone, wherein catalyst is separated from the product (II) or the product (IV) by extraction with water and the aqueous phase obtained is returned to the reaction zone, and wherein the extraction is carried out using part of the aqueous phase obtained in the rectification unit (III).

13. A process as claimed in claim 12, wherein the product (I) taken from the rectification unit (I) is fed to a rectification unit (II) and in this is separated into a product (V) comprising remaining 2-ethylhexanol, (meth)acrylic acid and components having boiling points lower than that of 2-ethylhexyl (meth)acrylate, 2-ethylhexyl (meth)acrylate and a product (VI) having a boiling point higher than that of 2-ethylhexyl (meth)acrylate.

14. A process as claimed in claim 13, wherein the product (V) is returned to the reaction zone, wherein the product (VI) is returned to the rectification unit (I), wherein the rectification unit (II) is a rectification column (II), and wherein the product (V) is separated off in the upper part of the rectification column (II), the product (VI) is taken from the bottom of the rectification column (II) and the 2-ethylhexyl (meth) acrylate is taken off in vapor form at the side in the lower part of the rectification column (II).

15. A process as claimed in claim 1, wherein part of the organic phase obtained in the rectification unit (III) is discharged to bleed off low-boiling by-products.

16. A process as claimed in claim 2, wherein the temperature in the first reaction region is 80–130° C., and in the last region is 110–130° C., and rises along the cascade.

17. A process as claimed in claim 2, wherein the pressure in all reaction regions is from 200 mbar to 700 mbar, and is the same in all reaction regions.

18. A process as claimed in claim 1, wherein the total residence time of the reactants in the reaction regions is from 1 to 7 hours, wherein the residence time decreases in successive reaction regions.

19. A process as claimed in claim 1, wherein the total residence time of the reactants in the reaction regions is from 2 to 5 hours, and wherein the residence time decreases in successive reaction regions.

20. A process as claimed in claim 1, wherein the catalyst used is paratoluenesulfonic acid, and wherein the content of catalytically active acid in the reaction zone, based on the reaction mixture present therein, is from 0.1 to 6% by weight of para-toluenesulfonic acid, and wherein the content of catalytically active acid in the liquid phase of the rectification unit I, based on the mixture present therein, is from 2.5 to 50% by weight of paratoluenesulfonic acid.

21. A process as claimed in claim 10, wherein the rectification unit (I) is a rectification column (I), the product mixture discharged from the reaction zone is fed to the lower part of the rectification column (I), the product (II) is obtained at the bottom of the rectification column (I) and the product (I) is obtained at the top of the rectification column (I), and wherein part of the product (II) is returned to the reaction zone in the first reaction region, either directly or via the rectification unit (III).

22. A process as claimed in claim 13, wherein the product (V) is returned to the reaction zone in the second reaction region, wherein the product (VI) is returned to the rectification unit (I), wherein the rectification unit (II) is a rectification column (II), and wherein the product (V) is separated off in the upper part of the rectification column (II), the product (VI) is taken from the bottom of the rectification column (II) and the 2-ethylhexyl (meth)acrylate is taken off in vapor form at the side in the lower part of the rectification column (II).

* * * * *